United States Patent
Colclough

(12) 
(10) Patent No.: US 6,303,557 B1
(45) Date of Patent: Oct. 16, 2001

(54) FAST ACTING DISINFECTANT AND CLEANER CONTAINING A POLYMERIC BIGUANIDE

(75) Inventor: Vanessa Louise Colclough, Fleet (GB)

(73) Assignee: S. C. Johnson Commercial Markets, Inc., Sturtevant, WI (US)

( * ) Notice: Subject to any disclaimer, the term of this patent is extended or adjusted under 35 U.S.C. 154(b) by 0 days.

(21) Appl. No.: 09/441,528

(22) Filed: Nov. 16, 1999

(51) Int. Cl.$^7$ ................................ C11D 3/48; C11D 1/62
(52) U.S. Cl. .................. 510/382; 510/199; 510/238; 510/247; 510/319; 510/341; 510/356; 510/384; 510/391; 510/432; 510/480; 510/490; 510/504; 510/533
(58) Field of Search ....................... 510/199, 238, 510/247, 319, 341, 356, 382, 384, 391, 432, 480, 490, 504, 533

(56) References Cited

U.S. PATENT DOCUMENTS

| | | | |
|---|---|---|---|
| 2,388,614 | 11/1945 | Kirby et al. | 167/22 |
| 3,751,370 | 8/1973 | Stimberg et al. | 252/102 |
| 4,264,479 | 4/1981 | Flanagan | 252/524 |
| 4,443,363 | 4/1984 | Klinger et al. | 252/547 |
| 4,456,543 | 6/1984 | Owens | 252/106 |
| 4,499,077 | 2/1985 | Stockel et al. | 424/149 |
| 4,661,523 | * 4/1987 | Disch et al. | 514/635 |
| 4,836,986 | * 6/1989 | Ogunbiyi et al. | 422/28 |
| 5,000,867 | 3/1991 | Heinhuis-Walther et al. | 252/106 |
| 5,030,659 | * 7/1991 | Bansemir et al. | 514/635 |
| 5,049,383 | 9/1991 | Huth et al. | 424/405 |
| 5,141,803 | * 8/1992 | Pregozen | 428/288 |
| 5,454,984 | 10/1995 | Graubart et al. | 252/547 |
| 5,527,506 | 6/1996 | Hamilton | 422/18 |
| 5,529,713 | * 6/1996 | Gauthier-Fournier | 252/106 |
| 5,668,084 | * 9/1997 | Unhoch et al. | 504/158 |
| 5,739,168 | * 4/1998 | Hioki et al. | 514/643 |
| 5,746,838 | * 5/1998 | Huth | 134/27 |
| 5,814,591 | 9/1998 | Mills et al. | 510/238 |
| 5,922,693 | 7/1999 | Oldenhove | 514/63 |
| 5,942,217 | * 8/1999 | Woo et al. | 424/76.1 |

FOREIGN PATENT DOCUMENTS

| | | | |
|---|---|---|---|
| 56592/73 | 8/1972 | (AU) | C11D/1/66 |
| 35 28 209 A1 | 4/1986 | (DE) | |
| 0 041 448 A1 | 12/1981 | (EP) | |
| 0087049 | 2/1983 | (EP) | A01N/59/00 |
| 0 099 209 A1 | 1/1984 | (EP) | |
| 0099209 | 1/1984 | (EP) | A01N/47/44 |
| 0 185 970 A1 | 7/1986 | (EP) | |
| 0226081B1 | 11/1986 | (EP) | A01N/47/44 |
| 0 226 081 A1 | 6/1987 | (EP) | |
| 0252310 | 6/1987 | (EP) | A01N/33/12 |
| 0361301 | 9/1989 | (EP) | A01N/47/44 |
| 0774504A1 | 5/1997 | (EP) | C11D/3/00 |
| 0 827 691 A1 | 3/1998 | (EP) | |
| 2 695 297 A1 | 3/1994 | (FR) | |
| 2 710 919 A1 | 4/1995 | (FR) | |
| 1355636 | 6/1974 | (GB) | A61L/13/00 |
| WO 98/47359 | 10/1998 | (WO) | A01N/33/12 |

OTHER PUBLICATIONS

Private correspondence from Zeneca Biocides dated Apr. 16, 1999 concerning Vantocil®IB antimicrobial product.

Diane K. Wyosowski R.N., "Epidemic Neonatal Hyperbilirubinemia and Use of a Phenolic Disinfectant Detergent" Pediatrics, vol. 61 No. 2, pp. 165–170, Feb. 1978.

Guinter Kahn M.D., "Depigmentation Caused by Phenolic Detergent Germicides", Arch Derm, vol. 102, pp. 177–187, Aug 1970.

"Cleaning Solutions Cause Skin Pigment Loss in Hospital Employees", JAMA, vol. 213 No. 4, pp. 535, 540, Jul. 27, 1970.

Helen Mck. Doan, PhD "Phenol and Neonatal Jaundice", Pediatrics vol. 64 No. 3, p. 324, Sep. 1979.

Larry L. Needham "Determination of Three Germicidal Phenols in Serum of Infants with Hyperbilirubinemia" Clinica Chimica Acta, vol. 107, pp. 261–266, 1908.

* cited by examiner

Primary Examiner—Mark Kopec
Assistant Examiner—Charles Boyer
(74) Attorney, Agent, or Firm—S. C. Johnson Commercial Markets, Inc.

(57) ABSTRACT

A cleaning and biocidal composition in liquid form comprising a solvent, a polymeric biguanide, a single quaternary ammonium salt, a sequestrant, and at least one surfactant. The composition comprising the solvent including water, the polymeric biguanide including a polyhexamethylene biguanide hydrochloride, the quaternary ammonium salt including a didecyldimethyl ammonium chloride, the sequestrant including an amino acid chelating agent selected from the group consisting of: ethylenediaminetetraacetic acid, nitrilotriacetic acid, tetrasodium ethylenediaminetetraacetic acid, or mixtures thereof, the surfactant including a non-ionic surfactant and an amphoteric surfactant.

13 Claims, No Drawings

FAST ACTING DISINFECTANT AND CLEANER CONTAINING A POLYMERIC BIGUANIDE

BACKGROUND OF THE INVENTION

1. Technical Field

The present invention relates generally to a composition that can be used for cleaning and disinfecting a hard surface in one step with a relatively short contact time. More particularly, it relates to a composition that will clean and disinfect a surface by killing 99.999% of bacteria in under five minutes. This is accomplished while still keeping the amount of expensive ingredients such as quaternary ammonium compounds and polymeric biguanide, each contained in the composition at low levels of at least 5 ppm in a diluted form or when diluted from a concentrated form.

2. Background Art

The cleaning and disinfecting of hard surfaces is important in both residential and commercial settings. The increasing importance of hygiene combined with the fast moving pace of the modem world has created a need for products with fast cleaning and disinfecting action. The main concerns are to effectively reduce bacteria in the short span of time the product is permitted to contact the surface while still maintaining a reasonable cost for the product allowing it to be feasible for commercial use. The use of a cleaner disinfectant concentrate in a liquid form is beneficial in that cleaning a surface and additionally elimination of bacteria is achieved in one step. The one step process reduces the bacteria that could cause contamination of other items placed on the surface such as food.

The European Union standard suspension test, European Norm 1276 (EN1276), is a standard test for evaluation of the effectiveness of biocides in the European Union. The test was designed to simulate dirty conditions allowing for the evaluation of results of a product, experienced with simultaneously cleaning and disinfecting. Organic soils and hard water are known to interfere with the activity of biocides, so the use of "interfering substances" namely, bovine albumin (0.3%) and hard water (300 ppm), represent the soil likely to be found when cleaning. The use of these interfering substances in the presence of quantitatively and qualitatively known bacteria (*pseudomonas aeruginosa*, the most difficult bacteria to kill; *esherichia coli; staphylococcus aureus; enteroccus hire;* amongst others) ensures a rigorous test standard ("dirty conditions"). To pass EN1276 and to claim a disinfectant product, a log 5 reduction (99.999% kill) of the bacteria must be attained at 20° C.

The use of Cleaner Disinfectant Concentrates is widespread throughout the industry, the majority being based on quaternary ammonium compounds. However, the kill of 99.999% of bacteria is normally met with long contact times (5 minutes or more) and by the use of products that contain very high levels of biocidal actives (much more than 300 ppm each). The consequence of using either a quaternary ammonium chloride or a polymeric biguanide alone is that they must be used in higher quantities to even achieve a satisfactory result at a time over five minutes. Additionally, the use of higher quantities results in a higher cost that is not commercially feasible. Polymeric biguanide is a particularly expensive biocide. The use of combinations of biocides until now has been ineffective in reducing the time necessary to eliminate 99.999% of the bacteria in the EN1276 test. The kill times have remained 5 minutes, which is excessive for the elimination of bacteria in a commercial setting or domestic setting because normal contact time of a cleaning an disinfecting composition within the work place or home is under five minutes.

U.S. Pat. No. 5,529,713 claims a cleaning and disinfectant solution that contains quaternary ammonium chlorides and biguanide hydrochloride. This patent teaches the use of two or more quaternary ammonium chlorides and biguanide hydrochloride. The patent also teaches the use of two different quaternary ammonium salts in combination and a biguanide hydrochloride in order to have an effective bacterial reduction after five minutes which is unacceptable in the settings the product will be used. This patent further teaches the use of isopropyl alcohol, which very volatile evaporating quickly and also extremely flammable. The patent lastly does not teach the use of a sequestrant in combination with the quaternary ammonium chlorides and the biguanide hydrochloride.

PCT patent publication WO 98/47359 describes a biocide composition without cleaning capabilities. The patent teaches the use of one quaternary ammonium chloride in over one percent and an amount of biguanide or another quaternary ammonium three percent or over in order to reduce bacteria in over five minutes. The patent also teaches the use of a high level of the biguanide or quaternary ammonium chloride is used without a sequestrant, in order to reduce a broad spectrum of bacteria that may be present.

Sales information distributed by Zeneca Biocides, 1800 Concord Pike Wilmington, Del. 19850, suggests the combination of quaternary ammonium salts and a polymeric biguanide compound at a high percentage and at a ratio of 2:1 in order to have broad range bacterial reduction. The information is presented in relation to their product "Vantocil" that is a biguanide solution.

SUMMARY OF INVENTION

The present invention relates to disinfecting a hard surface in a reduced amount of time. The preferred embodiment relates to the simultaneous cleaning and disinfecting of a hard surface in a reduced amount of time. The invention comprises a composition that provides bacterial kill in the order of 99.999% in less than five minutes by incorporating an effective combination of a polymeric biguanide and a quaternary ammonium in effective amounts of at least 5 ppm and most preferably at 100 ppm to 300 ppm each of the total composition, with a sequestrant all in diluted form. In addition the invention is a broad range disinfectant that kills 99.999% of bacteria, including *pseudomonus aeruginosa*, passing the EN1276 bacteria test method under "dirty" conditions in just 30 seconds.

One aspect of the invention relates to a composition that contains a biocide and a cleaner in a liquid form that comprises a solvent, a polymeric biguanide, a quaternary ammonium compound, a sequestrant, and one or more surfactants. The preferred composition employs a solvent that includes water, a polyhexamethylene biguanide as the polymeric biguanide, and a didecyldimethylammonium as the quaternary ammonium. The composition also includes a sequestrant that is an acetic acid derivative selected from the group consisting of ethylenediaminetetraacetic acid (EDTA), nitrilotriacetic acid (NTA), Tetrasodium EDTA, or mixtures thereof. The surfactants contained in this composition comprise a linear alcohol ethoxylate and an amphoteric betaine. The composition contains the polymeric biguanide, quaternary ammonium salt, and a sequestrant of ethylenediaminetetraacetic acid (EDTA), nitrilotriacetic acid (NTA), Tetrasodium EDTA or a mixture thereof in a ratio of 1 to 3:1 to 3:1 to 3 most preferred in a ratio of 1:1:1.

Another aspect of the invention comprises a composition that contains a biocide with a cleaner in a diluted liquid form that comprises water as a solvent, a polymeric biguanide that is at least 5 ppm of the total composition, a quaternary ammonium salt that is at least 5 ppm, of the total composition, sequestrant that is at least 5 ppm of the total composition, one or more surfactant that is at least 5 ppm of the total composition. The polymeric biguanide, preferably polyhexamethylene biguanide, and the quaternary ammonium salt, preferably didecyldimethylammonium, are contained in approximately equal amounts and preferably each presented in at least 100 ppm in the total composition.

The invention also comprises a composition containing a biocide and a cleaning composition in a diluted liquid form containing a solvent of water, a polyhexamethylene biguanide and a didecyldimethylammonium chloride in approximately equal amounts of at least 5 ppm each of the total composition, a tetrasodium EDTA in at least 5 ppm of the total composition, a 9 carbon atom–11 carbon atom linear alcohol ethoxylate containing 6 moles ethylene oxide and an alkyl amido propyl dimethyl amine betaine in a combination in at least 5 ppm of the total composition. The composition incorporates a method for cleaning and disinfecting a hard surface that reduces kill time of *pseudomonas aeruginosa* bacteria to 30 seconds: wherein the concentrated composition is diluted 1:100, then applied to a hard surface allowed to stand for fewer than 5 minutes and then the composition is removed eliminating 99.999% of bacteria, including the *pseudomonas aeruginosa,* on the surface.

Another aspect of the invention relates to a biocide and cleaning composition containing a polymeric biguanide, a quaternary ammonium salt, in a ratio of approximately 1:1 and, tetrasodium EDTA, in amounts effective to reduce *pseudomonas aeruginosa* bacteria in 30 seconds or less, using the EN1276 test method under "dirty" conditions.

The invention further comprises a concentrated composition that contains a biocide with a cleaner in a liquid form that comprises water as a solvent, a polymeric biguanide that is at least 5 ppm when diluted, quaternary ammonium salt that is at least 5 ppm when diluted, sequestrant that is at least 5 ppm when diluted, one or more surfactant that is at least 5 ppm when diluted.

The biocide elements of the composition that are the quaternary ammonium, the polymeric biguanide, and the sequestrant, are contained in a ratio about 1:1:1 respectfully. The ratio of the biocides is maintained in a concentrated form or a diluted form.

DETAILED DESCRIPTION OF THE INVENTION

The purpose of the invention is to produce a composition for a concentrated cleaner disinfectant for the purpose of cleaning and disinfecting hard surfaces, in a shorter period of time (demonstrated through fast kill times in the EN1276) than known to date, while still meeting the commercial and regulatory requirements by using lower levels of biocides. The problem in prior compositions was the kill time was over five minutes and any attempts to lower this time involved the use of large amounts of the biocides which were unacceptable for their increased in cost.

In the present invention the purpose was accomplished while simultaneously meeting the commercial and regulatory requirements while still maintaining low amount of biocide in the composition. Using a combination of a single quaternary ammonium salt with a single polymeric biguanide and a single sequestrant solved the problem described above, on which the invention is based. The combination of these elements in lower concentration provides a synergy that allows for the exponential increase in effectiveness and speed of bacterial elimination. This increased efficacy is enough to reduce the kill time from 5 minutes to 30 seconds while still reducing *pseudomonas aeruginosa* and other bacteria by 99.999% in the EN1276 test under dirty conditions. This effect is not seen when either of the biocides are used alone or if the combination of the two or more biocides are used without the sequestrant. The combination of all three compounds is the key factor in the invention. An illustration of the benefits of the claimed composition over standard compositions is detailed below.

The present composition of the invention solves the problem by incorporating a polymeric biguanide having the general structure of:

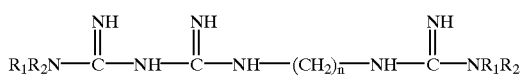

Where R1 is an alkyl, or an aminoalkyl radical, R2 is a hydrogen atom or an alkyl radical and n is an integer from 1–6. The amount of the biguanide is at least 5 ppm in the diluted form. The preferred range is 100 ppm to 300 ppm in the diluted form. The reason for the preferred range is because the level is low enough to make the composition economically feasible and cause no environmental hazard while still reducing the kill rate to 30 seconds. The ranges of the polymeric biguanide in the concentrated form is an effective amount of at least 5 ppm when diluted. The preferred biguanide is polyhexamethylene biguanide and has the structure with n being 12:

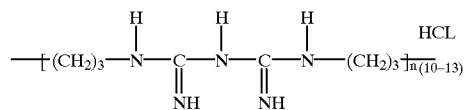

The biguanide is contained in the amount of at least 5 ppm of the total diluted composition and more preferred at a level of 100 ppm to 300 ppm when diluted. The preferred amount and specific biguanide allows for the greatest effectiveness with the other products contained within the claimed invention.

The present composition of the invention also claims a quaternary ammonium salt that has the general structure of:

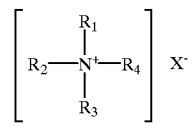

Where R1 and R2 are a CH3 or alkyl group containing 6 to 22 carbon atoms. R3 and R4 are alkyl groups which can be either an aromatic ring or a straight or branched carbon chain containing 6 to 22 carbon atoms and X is an anion selected from the following group: halogen, acetate, phosphate, nitrate, and sulfate. The amount of the biguanide is at least 5 ppm in the diluted form. The preferred range is 100 ppm to 300ppm in the diluted form. The reason for the preferred range is because the level are low enough to make the economically feasible and cause no environmental hazard while still reducing the kill rate to 30 seconds. The ranges of the quaternary ammonium in the concentrated form is at least 5 ppm when diluted. The preferred quaternary ammonium is didecyldimethylammonium that has the structure:

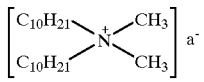

Where there are two methyl groups and there are two decyl groups (10 carbon atoms). The quaternary ammonium is contained in the composition in at least 5 ppm of the total composition and at the more preferred range of 100 ppm to 300 ppm. The preferred quaternary compound and its preferred amount allows for the greatest effectiveness with the other products contained within the claimed invention when within the range of the invention.

The combination of quaternary ammonium with the polymeric biguanide allow for the broad spectrum of bacterial elimination of gram negative and gram positive bacteria. The broad spectrum is not at the efficiency level that is needed to product results in a short period of time. To increase the efficiency a sequestrant is added to the formulation to increase the elimination ability and speed of the biocides. The sequestrant that can be used has the general structures:

1) EDTA

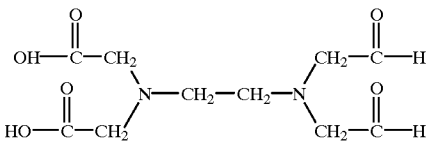

2) NTA

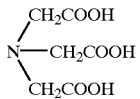

The amount of the sequestrant is at least 5 ppm in the diluted form. The preferred range of the sequestrant at 100 ppm to 1000 ppm in the diluted form. The reason for the preferred range is because the level is high enough to assist in the formulation and increase the efficacy of the biocides reducing the kill rate to 30 seconds. The ranges of the sequestrant in the concentrated form is an effective amount of at least 5 ppm when diluted. The preferred sequestrant is tetrasodium ethylenediaminetetraacetic acid that has the structure:

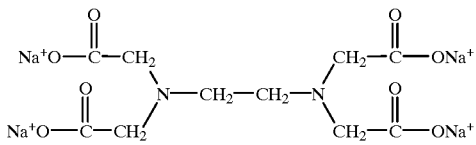

The combination of a single quaternary ammonium, the polymeric biguanide and the sequestrant allow for the broad spectrum of bacterial elimination of gram negative and gram positive bacteria and additionally dramatically reduce the kill time require for the bacterial elimination. The composition further includes surfactants that are added so that there is a combined cleaning and disinfecting process. The surfactants are selected from group that allows for the maximum cleaning effect and minimal interference with the ability of the biocides to work properly. The surfactant is one or more from the following general structures.

1) 
$R(OCH_2-CH_2)_nOH$   alcohol ethoxylate

2) 
$$R(OCH\underset{|}{\overset{CH_3}{{}}}-CH_2)_nOH$$   alcohol propoxylate

3) 
$$R(OCH_2CH_2)_x(\underset{|}{\overset{CH_3}{{}}}CH_2CH_2-O)_YH$$   mixed ethoxylate/propoxylate Where R is an alkyl derivative containing a reactive hydrogen atom for example an alkyl phenol, alcohol, amine, fatty acid, ester, glyceride or amide. The carbon chain length can vary from 6 carbon atoms to 18 carbon atoms. Also, n is 3 to 5 moles of ethoxylation or propoxylation, x is 3 to 15 moles ethoxylation and y is 2 to 4 moles propoxylation.

4) 
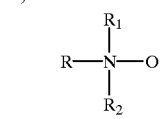

amine oxide

Where R is an alkyl group having 10 to 16 carbon atoms, R1 and R2 are identical or different alkyl groups but are often CH3.

5) 
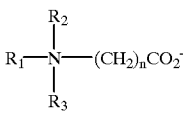

amphotericbetaine

Where R1 is an alkyl group having 10 to 16 carbon atoms, R2 and R3 are identical or different alkyl groups having 1 to 4 carbon atoms, n is integers from 1 to 18.

6) 
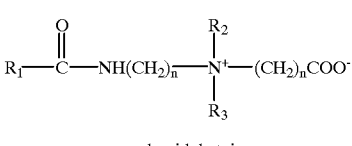

propylamidobetaine

Where R1 is an alkyl group having 10 to 16 carbon atoms, R2 and R3 are identical or different alkyl groups having 1 to 4 carbon atoms, n is integers from 1 to 18.

$RNHCH_2CO_2H$ glycinate     7)

Where R is an alkyl group having 1 to 4 carbon atoms. The surfactants have an amount of at least 5 ppm of the total composition in diluted form. The preferred range of 5 ppm to 3000 ppm, which allows for the most effective cleaning while still not interfering with the effectiveness of the biocides to kill bacteria. If the surfactants are used in too high quantities then the will inhibit the effectiveness of the biocides and the sequestrants and reduce or eliminate their bacterial reduction effects. The ranges of the surfactant in the concentrated form is an effective amount of at least 5 ppm.

The solvent in the present invention can be a liquid that is environmentally acceptable, non-irritating to humans, will dissolve the ingredients and is not so volatile that it will evaporate before allowing the ingredients to clean the surface. The solvent is added to present composition of the invention to bring it up to 1,000,000 ppm or 100% in its concentrated state and diluted state. The solvent can be water, alcohol (ethanol, isopropyl), or glycols. The preferred solvent is water because it does not interfere with the effectiveness of the surfactants or the biocides and sequestrant.

The determination of bacterial kill of the cleaning and biocidal agent was evaluated using The European Union standard suspension test, European Norm 1276 (EN1276). This is a standard test for evaluation of the effectiveness of biocides in the European Union. The test was designed to simulate the dirty conditions experienced when simultaneous cleaning and disinfecting occurs. Organic soils and hard water are known to interfere with the activity of biocides, so the use of "interfering substances" namely, bovine albumin (0.3%) and hard water (300 ppm), represent the soil likely to be found when cleaning. The use of these interfering substances in the presence of quantitatively and qualitatively known bacteria (*pseudomonas aeruginosa; esherichia coli; staphylococcus aureus; enteroccus hire;* amongst others) ensures a rigorous test standard ("dirty conditions"). To pass the EN1276 and to claim a disinfectant product, a log 5 reduction (99.999% kill) of the bacteria must be attained in five minutes at 20° C. The EN1276 test method can also be used to test the effectiveness of disinfecting products when using contact times shorter than 5 minutes.

EXAMPLE 1

A cleaning composition was prepared according to the present invention containing water as a solvent and combining into the solvent first, 180 ppm of tetrasodium ethylenediaminetetraacetic acid, second, 600 ppm linear alcohol ethoxylate and 30 ppm betaine, third, 180 ppm of polymeric biguanide, and finally 180 ppm of a quaternary ammonium. The composition was tested and passed the EN1276 under dirty conditions, on all bacteria including *pseudomonas aeruginosa* in just 30 seconds. (as shown in table 1).

EXAMPLE 2

The composition used for example 2, contained 220 ppm polymeric biguanide as the only biocide (having a comparable cost to composition A) failed the EN1276, dirty conditions, on *pseudomonas aeruginosa* in 5 minutes. In order to attain a pass at 5 minutes, let alone 30 seconds the level of biguanide would need to be increased to a level that is unacceptable due to environmental issues and commercial feasibility. (as shown in table 1).

EXAMPLE 3

A composition containing 720 ppm of quaternary ammonium salt with no biguanide, was tested per the EN1276, on *pseudomonas aeruginosa* in 5 minutes it failed as shown in table 1. Increasing this concentration up to 960 ppm passed the EN1276, on *pseudomonas aeruginosa* in 5 minutes. Again to pass the EN1276 in 30 seconds the quaternary ammonium salt would need to be increased to a level to which commercial feasibility and environmental acceptability are reduced, other aspects of the composition optimized in composition A, such as cleaning, would be decreased by the increase in the biocide (as shown in table 1).

The test is conducted in a controlled environment where the bacteria are cultured in bovine serum. After the bacteria is cultured there is a count made of the bacteria to establish if there is a large enough count to perform the testing. Once there is a sufficient count the composition is applied and removed allowing for testing at different time intervals. After the desired time has passed and the composition is neutralized or filtered, the resultant solution cultured and a final count is performed to establish if the bacteria count was reduced sufficiently for a passing result. To conclude there was a passing result the bacteria count must be lowered by a log 5 reduction, or 99.999%. The results in the EN1276 testing at 30 seconds are as follow in table one.

The compositions tested show the increases in the effectiveness and the reduction in the time needed for bacterial kill. The use of a quaternary ammonium salt, a polymeric biguanide with tetrasodium EDTA in combination is key to eliminating the need for higher levels of biocide to kill bacteria in a short contact time.

TABLE I

Results: EN1276 test under dirty conditions at a 1:100 dilution.

| NAMES | EXAMPLE 1 | EXAMPLE 2 | EXAMPLE 3 |
|---|---|---|---|
| CONTENTS IN DILUTED FORM: | | | |
| BIGUANIDE (100%) | 180 PPM | 220 PPM | 0 PPM |
| QUATERNARY AMMONIUM (100%) | 180 PPM | 0 PPM | 720 PPM |
| TETRASODIUM EDTA (100%) | 180 PPM | 220 PPM | 320 PPM |
| LINEAR ALCOHOL ETHOXYLATE (100%) | 600 PPM | 600 PPM | 600 PPM |
| BETAINE (100%) | 30 PPM | 30 PPM | 0 PPM |
| DI WATER | TO 100% | TO 100% | TO 100% |
| EN 1276 TEST RESULTS AT 30 SECONDS | PASS | FAILED | FAILED |
| EN 1276 TEST RESULTS AT 5 MINUTES | PASS | FAILED | FAILED |

What is claimed is:

1. A biocidal composition in liquid form comprising:
    a) a solvent;
    b) at least 5 ppm of the total composition of a polymeric biguanide;
    c) at least 5 ppm of the total composition of a quaternary ammonium salt; and
    d) at least 5 ppm of the total composition of a sequestrant; wherein the ratio of components b, c and d is approximately (1–3):(1–3):(1–3).

2. A cleaning and biocidal composition in liquid form comprising:
    a) water,
    b) at least 5 ppm of the total composition of a polymeric biguanide;
    c) at least 5 ppm of the total composition of a quaternary ammonium salt;
    d) at least 5 ppm of the total composition of a sequestrant; and e) at least 5 ppm of the total composition of a cleaning agent comprising at least one surfactant;

wherein the ratio of components b, c and d is approximately (1–3):(1–3):(1–3).

3. The cleaning and biocidal composition of claim 2 wherein the quaternary ammonium salt and polymeric biguanide are in an amount of at least 100 ppm of the total composition.

4. The cleaning and biocidal composition of claim 2 wherein the quaternary ammonium salt, the polymeric biguanide and the sequestrant are in a ratio of approximately 1 to 1 to 1.

5. The cleaning and biocidal composition of claim 2 wherein the polymeric biguanide includes a polyhexamethylene biguanide hydrochloride.

6. The cleaning and biocidal composition of claim 2 wherein the quaternary ammonium salt includes a didecyldimethyl ammonium chloride.

7. The cleaning and biocidal composition of claim 2 wherein the sequestrant includes an amino acid chelating agent selected from the group consisting of: ethylenediaminetetraacetic acid, nitrilotriacetic acid, tetrasodium ethylenediaminetetraacetic acid, or mixtures thereof.

8. The cleaning and biocidal composition of claim 2 wherein the one or more surfactant includes a non-ionic surfactant and an amphoteric surfactant.

9. The cleaning and biocidal composition of claim 8 wherein the non-ionic surfactant includes linear ethoxylated alcohol with a linear or branched carbon chain length between 8 carbon atoms and 18 carbon atoms and 1 to 10 moles of ethylene oxide and the amphoteric surfactant includes a betaine with a linear or branched carbon chain between 8 carbon atoms and 18 carbon atoms.

10. A cleaning and biocidal composition in liquid form according to claim 2 additionally comprising a 9 carbon atom–11 carbon atom linear alcohol ethoxylate containing 6 moles ethylene oxide and an alkyl amido propyl dimethyl betaine in a combination of at least 5 ppm of the total composition.

11. A method for disinfecting a hard surface comprising applying a biocide composition, which comprises a polymeric biguanide, a quaternary ammonium compound, tetrasodium ethylenediaminetetraacetic acid, in a ratio of approximately (1–3):(1–3):(1–3) and optionally containing a cleaning agent wherein the composition is applied to a surface permitting the composition to remain in contact with the surface for 5 minutes or less and then removing the composition thereby eliminating substantially all bacteria, including *pseudomonas aeruginosa,* on the surface.

12. The method of claim 11 wherein the composition is diluted with a solvent before application to the hard surface.

13. The cleaning and biocidal composition of claim 10 wherein the polymeric biguanide, the quaternary ammonium salt, and the sequestrant are in a ratio of approximately 1:1:1.

* * * * *